United States Patent [19]

Muthmann

[11] Patent Number: 5,086,448
[45] Date of Patent: Feb. 4, 1992

[54] X-RAY EXAMINATION UNIT

[76] Inventor: Karl-Dieter Muthmann, Siegfriedstrasse 5, D 5810 Witten, 10 Witten

[21] Appl. No.: 455,297
[22] Filed: Dec. 22, 1989
[51] Int. Cl.⁵ ............................................. H05G 1/02
[52] U.S. Cl. ................................... 378/197; 378/196; 378/193; 378/167
[58] Field of Search ............... 378/193, 195, 196, 197, 378/198, 208, 209, 155, 179, 20, 17, 21, 154, 152, 167, 11, 19, 189

[56] References Cited

U.S. PATENT DOCUMENTS

| | | | |
|---|---|---|---|
| 3,803,417 | 4/1974 | Kok | 378/197 |
| 4,503,552 | 3/1985 | Miyahara et al. | 378/197 |
| 4,653,083 | 3/1987 | Rossi | 378/195 |
| 4,879,737 | 11/1989 | Grady | 378/195 |
| 4,922,512 | 5/1990 | Lajus et al. | 378/195 |
| 4,987,585 | 1/1991 | Kidd et al. | 378/193 |

Primary Examiner—Janice A. Howell
Assistant Examiner—Don Wong
Attorney, Agent, or Firm—Bruce L. Adams; Van C. Wilks

[57] ABSTRACT

The invention relates to a X-ray examination unit, comprising a stand on which is vertically movable a bracket with a moving grid means and a X-ray tube. In order to permit a large number of photographing possibilities on a standing, sitting or lying patient from different directions, said bracket is also horizontally movable, said moving grid means at a lateral end of said bracket is pivotable about a vertical axis, said X-ray tube is held on one end of a substantially C-shaped support arm, whose other end is located on said moving grid means and is fixed in such a way that said X-ray tube, together with said moving grid means, is pivotable about said vertical axis and said moving grid means is additionally rotatable about a horizontal axis.

3 Claims, 2 Drawing Sheets

5,086,448

X-RAY EXAMINATION UNIT

BACKGROUND OF THE INVENTION

The invention relates to an X-ray examination unit with a stand on which is vertically movable a bracket with a moving grid means and an X-ray tube.

Particularly for radiographs or screening and flouroscopy respectively of horizontally positioned patients, it is important in emergency medicine that X-ray examination units are available which allow to obtain radiographs and fluoroscopy pictures of the patient lying on the patient support, without it being necessary to move the body of the possibly unconscious patent into a different position for this purpose. Thus, the moving grid means and the X-ray tube must be so positioned with respect to the patient as to permit a large number of different shots from different directions. Heretofore a considerable expenditure has been involved in obtaining such versatile X-ray examination units. Thus, there is a need for such a versatile unit having a construction which, measured against its versatility, can be manufactured with limited effort and expenditure and can be relatively easily operated.

SUMMARY OF THE INVENTION

According to the invention this need is satisfied by an X-ray examination unit including a stand on which is vertically movable a bracket with a moving grid means and an X-ray tube, characterized by that said bracket is also horizontally movable on said stand, said moving grid means is so pivotably mounted about a vertical axis at one of the lateral ends of said bracket, such that it is pivotable at least between a front position in front of said bracket and a lateral position beside said bracket removed therefrom by a pivot angle of about 90°, said X-ray tube is held on one end of a substantially C-shaped support arm, whose other end is arranged on said moving grid means in such a way that said X-ray tube is located in a photographing position with respect to said moving grid means and is pivotable together with the latter about said vertical axis and said moving grid means and said other end of said support arm are rotatable with respect to said bracket about a horizontal axis, either jointly as a unit, or separately and independently of one another.

As a result of the both horizontal and vertical mobility of the bracket mounted in corresponding guides on a stand, as well as in particular due to the pivotability of the moving grid means and the X-ray tube held by means of the roughly C-shaped support arm with a corresponding moving grid means arrangement, as well as the rotatability of both the moving grid means and the support arm with the X-ray tube about a horizontal axis with respect to the bracket, a heretofore unattainable versatility of the arrangement of the X-ray tube and moving grid means with respect to a patient lying on the patient table is obtained.

Apart from the radiographs and screenings of sitting and standing patients possible with existing units, it is now in particular possible to take lateral or shots radiographic exposures of patients in a horizontal position. For achieving the latter the moving grid means is positioned vertically alongside the particular end face of the bracket and the X-ray tube is held by means of the C-shaped support arm at a corresponding distance opposite the moving grid means, so that it is possible to take lateral photographs of the patient, who is e.g. lying on an appropriate table moved to the stand and who then, viewed from above, is located between the vertically positioned moving grid means and the X-ray tube.

All other photographing possibilities result from the inventive features in conjunction with the standard technology used and are in particular apparent to persons skilled in the art through studying the attached drawing.

BRIEF DESCRIPTION OF THE DRAWINGS

The drawing of FIG. 1 diagrammatically shows in perspective form an embodiment of an X-ray examination unit according to the invention. The drawing of FIG. 2 diagrammatically shows a side view of an embodiment of an X-ray unit according to the invention.

DETAILED DESCRIPTION OF THE INVENTION

Figure 1:
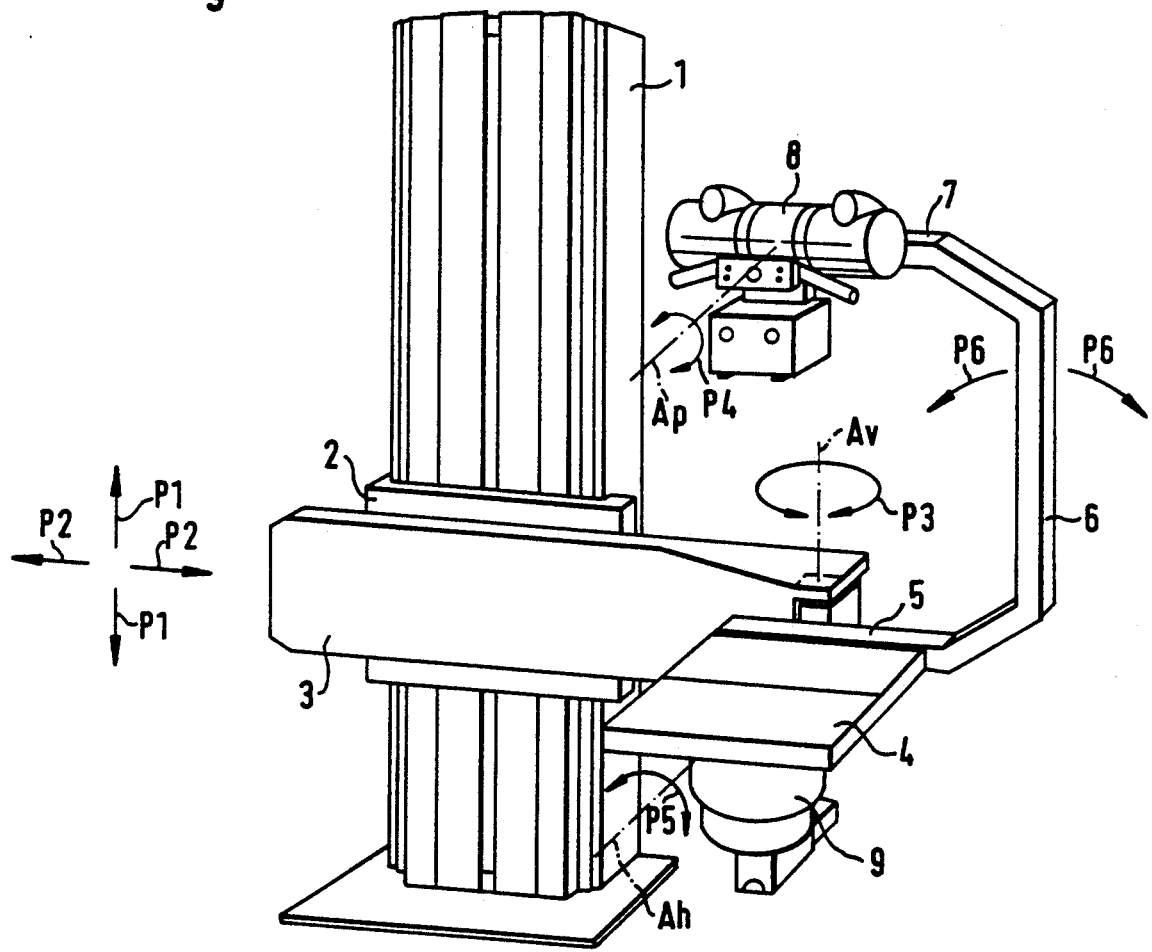
Figure 2:
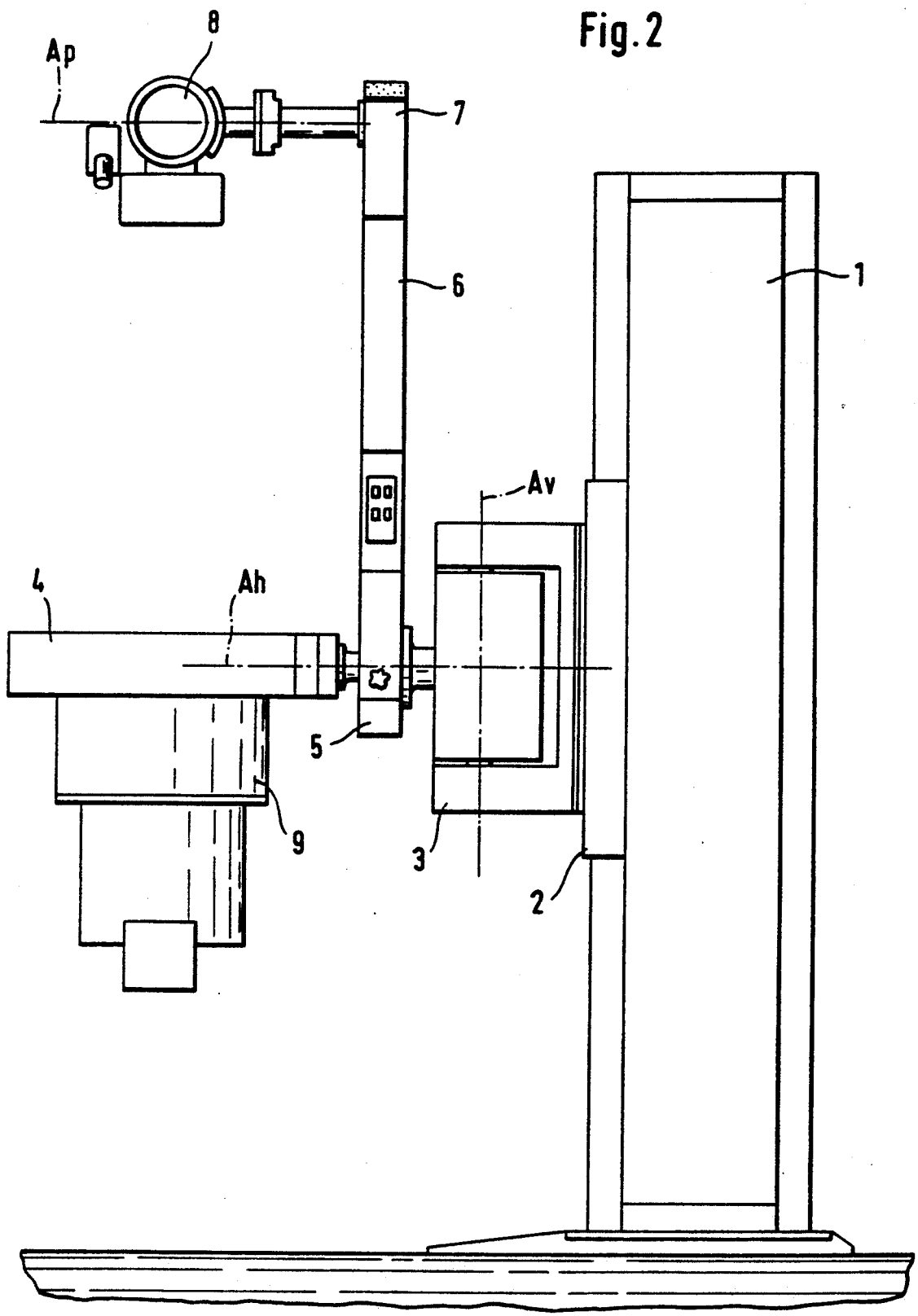

As indicated by arrow Pl, a support plate 2 is vertically movable by means of conventional guides (not shown) and drives on a column 1 which is either fixed to the wall or is free-standing with a corresponding floor fastening in the examination room.

On the support plate 2 is horizontally movably located a bracket 3 by means of precision guides and drives (not shown) which are positioned between the support plate 2 and the bracket 3, as indicated by arrow P 2, so that photographs can be taken with digital image substraction.

At the right-hand and lateral end of bracket 3 in the drawing is provided a bearing means, by means of which a moving grid means 4 is pivotable about a vertical axis Av in the represented arrangement. The pivot angle, indicated by the double arrow P 3 is at least sufficiently large to enable the moving grid means 4 to be pivoted from the position shown in the drawings in front of bracket 3 into a not shown lateral position beside the bracket 3 and which corresponds to a pivot angle of 90°.

On the side of the moving grid means 4 facing the bracket 3 is fixed one end 5 of an approximately C-shaped support arm 6. To the opposite end 7 of the support arm 6 is fitted an X-ray tube 8, which can be pivoted about an axis Ap, as indicated by double arrow P4. Axis Ap is parallel to a horizontal axis Ah described hereinafter.

The mounting of the on moving grid means 4 on bracket 3 is such that it not only allows a pivoting movement of the grid means 4, support arm 6 and X-ray tube 8 as a unit about the vertical axis Av, but simultaneously the aforementioned components are mounted so as to rotate as a unit about a horizontal axis Ah, aided by a corresponding electromotive drive, the rotation angle being indicated by the double arrow P 5.

In the represented embodiment, the support arm 6 with the X-ray tube 8 by fixing to the moving grid means 4 is jointly rotatable therewith as a unit about the axis Ah. This ensures the maintenance of a once set spacing and also the parallelism between the moving grid means 4 and the X-ray tube 8.

However, diverging from the aforementioned, represented embodiment, it is also possible to arrange for the end 5 of the support arm 6 to rotate about axis Ah independently of the moving grid means 4, so that said relative rotatability of the support arm 6 and moving grid means 4 makes it possible to direct the X-ray tube 8 in a sloping manner and under an angle less than 90° respectively onto the image plane of the grid means 4. This independent rotatability of the arm 6 is indicated by an arrow P6.

From the drawings in conjunction with the above description, the one skilled in the art can gather the large number of different setting possibilities with respect to the standing, sitting and in particular lying patient.

It is in particular pointed out that the connection between the moving grid means 4 and the X-ray tube 8 need not necessarily be a C-shaped support arm. This was chosen in order to permit easy handling and in particular in order to create the necessary free space between the moving grid means 4 and the tube 8. It is also possible to use a support arm or some other connecting member with a different configuration.

The moving grid means 4 can be used in conjunction with any cassette, unlike a cassette case, whose use is limited to a single format. As shown by the drawings, the selected arrangement also permits the use of a moving grid means 4 in conjunction with an image intensifier, 9 at present up to a format of 40 cm (image intensifier entrance field format).

I claim:

1. An X-ray examination unit comprising:
   a stand,
   a bracket vertically and horizontally movable on said stand,
   moving grid means pivotably mounted about a vertical axis at one of the lateral ends of said bracket such that said moving grid means is pivotable at least between a front position in front of said bracket and a lateral position beside said bracket removed therefrom by a pivot angle of about 90°,
   an X-ray tube held on one end of a substantially C-shaped support arm, the other end of said support arm being arranged on said moving grid means in such a way that said X-ray tube is located in a photographing position with respect to said moving grid means and is pivotable together with said moving grid means about said vertical axis, and
   means mounting said moving grid means and said other end of said support arm for rotary movement with respect to said bracket about a horizontal axis, either jointly as a unit or singly and independently of one another.

2. An X-ray examination unit according to claim 1, wherein said X-ray tube is pivotable in two directions about an axis parallel to said horizontal axis of said rotary movement of said moving grid means and said other end of said support arm.

3. An X-ray examination unit according to claim 1, wherein said bracket is horizontally movable on a support plate mounted on said stand by means to enable photographs to be taken with digital image subtraction.

* * * * *